(12) United States Patent
Skujins et al.

(10) Patent No.: US 7,841,994 B2
(45) Date of Patent: Nov. 30, 2010

(54) MEDICAL DEVICE FOR CROSSING AN OCCLUSION IN A VESSEL

(75) Inventors: Peter Skujins, Minneapolis, MN (US); Brian R. Reynolds, Ramsey, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 11/934,673

(22) Filed: Nov. 2, 2007

(65) Prior Publication Data

US 2009/0118644 A1    May 7, 2009

(51) Int. Cl.
*A61M 25/09* (2006.01)
(52) U.S. Cl. .................................. 600/585
(58) Field of Classification Search ............ 600/585, 600/434, 435; 604/164.13, 523, 524, 526, 604/527
See application file for complete search history.

(56) References Cited

U.S. PATENT DOCUMENTS

| | | | |
|---|---|---|---|
| 1,553,227 A | 9/1925 | Feyk et al. | |
| 1,866,888 A | 7/1932 | Hawley | |
| 2,275,827 A | 3/1942 | Plensler | |
| 2,413,805 A | 1/1947 | Vickers | |
| 2,437,542 A | 3/1948 | Krippendorf | |
| 2,441,166 A | 5/1948 | Raspert | |
| 2,561,890 A | 7/1951 | Stoddard | |
| 2,722,614 A | 11/1955 | Fryklund | |
| 2,857,536 A | 10/1958 | Light | |
| 2,864,017 A | 12/1958 | Waltscheff | |
| 2,871,793 A | 2/1959 | Michie et al. | |
| 3,249,776 A | 5/1966 | Anderson et al. | |
| 3,322,984 A | 5/1967 | Anderson | |
| 3,334,253 A | 8/1967 | Hill | |
| 3,363,470 A | 1/1968 | Yavne | |
| 3,416,531 A | 12/1968 | Edwards | |
| 3,452,227 A | 6/1969 | Welch | |
| 3,452,742 A | 7/1969 | Muller | |
| 3,463,197 A | 8/1969 | Slade | |
| 3,463,953 A | 8/1969 | Maxwell | |
| 3,481,368 A | 12/1969 | Vansickle et al. | |

(Continued)

FOREIGN PATENT DOCUMENTS

AU           723040         12/1997

(Continued)

OTHER PUBLICATIONS

Webster's II New Riverside University Dictionary, ISBN 0-395-33957-X, 1994 p. 67.*

*Primary Examiner*—Max Hindenburg
*Assistant Examiner*—Michael C. Stout
(74) *Attorney, Agent, or Firm*—Crompton, Seager & Tufte, LLC

(57) ABSTRACT

The invention provides design, material, manufacturing method, and use alternatives for medical devices. An example medical device includes an elongated core member including an outer surface, an intermediate member disposed about at least a portion of the outer surface of the core member, and a coil disposed about at least a portion of the intermediate member in the distal region. At least a portion of an outer surface of the coil can include an undulating surface in a portion of the distal region.

28 Claims, 8 Drawing Sheets

U.S. PATENT DOCUMENTS

| | | | |
|---|---|---|---|
| 3,512,019 A | 5/1970 | Durand | |
| 3,544,868 A | 12/1970 | Bates | |
| 3,625,200 A | 12/1971 | Muller | |
| 3,686,990 A | 8/1972 | Margolien | |
| 3,731,671 A * | 5/1973 | Mageoh | 600/585 |
| 3,739,770 A | 6/1973 | Mori | |
| 3,841,308 A | 10/1974 | Tate | |
| 3,890,977 A | 6/1975 | Wilson | |
| 3,906,938 A | 9/1975 | Fleischhacker | |
| 3,924,632 A | 12/1975 | Cook | |
| 4,000,672 A | 1/1977 | Sitterer et al. | |
| 4,003,369 A | 1/1977 | Heilman et al. | |
| 4,020,829 A | 5/1977 | Willson et al. | |
| 4,030,503 A | 6/1977 | Clark, III | |
| 4,142,119 A | 2/1979 | Madey | |
| 4,215,703 A | 8/1980 | Wilson | |
| 4,279,252 A | 7/1981 | Martin | |
| 4,330,725 A | 5/1982 | Hintz | |
| 4,425,919 A | 1/1984 | Alston, Jr. et al. | |
| 4,430,083 A | 2/1984 | Ganz et al. | |
| 4,447,239 A | 5/1984 | Krutten | |
| 4,476,754 A | 10/1984 | Ducret | |
| 4,482,828 A | 11/1984 | Vergues et al. | |
| 4,484,586 A | 11/1984 | McMickle et al. | |
| 4,495,134 A | 1/1985 | Ouchi et al. | |
| 4,516,972 A | 5/1985 | Samson | |
| 4,545,390 A | 10/1985 | Leary | |
| 4,551,292 A | 11/1985 | Fletcher et al. | |
| 4,563,181 A | 1/1986 | Wijayarathna et al. | |
| 4,571,240 A | 2/1986 | Samson et al. | |
| 4,574,670 A | 3/1986 | Johnson | |
| 4,577,543 A | 3/1986 | Wilson | |
| 4,580,551 A | 4/1986 | Siegmund et al. | |
| 4,583,404 A | 4/1986 | Bernard et al. | |
| 4,635,270 A | 1/1987 | Gürs | |
| 4,636,346 A | 1/1987 | Gold et al. | |
| 4,657,024 A | 4/1987 | Coneys | |
| 4,665,906 A | 5/1987 | Jervis | |
| 4,676,249 A | 6/1987 | Arenas et al. | |
| 4,690,175 A | 9/1987 | Ouchi et al. | |
| 4,706,671 A | 11/1987 | Weinrib | |
| 4,719,924 A * | 1/1988 | Crittenden et al. | 600/585 |
| 4,721,117 A | 1/1988 | Mar et al. | |
| 4,737,153 A | 4/1988 | Shimamura et al. | |
| 4,762,130 A * | 8/1988 | Fogarty et al. | 606/159 |
| 4,763,647 A | 8/1988 | Gambale | |
| 4,764,324 A | 8/1988 | Burnham | |
| 4,774,949 A | 10/1988 | Fogarty | |
| 4,781,092 A | 11/1988 | Gaiser | |
| 4,781,186 A | 11/1988 | Simpson et al. | |
| 4,786,220 A | 11/1988 | Fildes et al. | |
| 4,790,331 A | 12/1988 | Okada et al. | |
| 4,800,890 A | 1/1989 | Cramer | |
| 4,811,743 A | 3/1989 | Stevens | |
| 4,813,434 A | 3/1989 | Buchbinder et al. | |
| 4,817,613 A | 4/1989 | Jaraczewski et al. | |
| 4,819,634 A | 4/1989 | Shiber | |
| 4,827,941 A | 5/1989 | Taylor et al. | |
| 4,830,023 A | 5/1989 | De Toledo et al. | |
| 4,831,858 A | 5/1989 | Yoshizawa | |
| 4,832,047 A | 5/1989 | Sepetka et al. | |
| 4,846,186 A | 7/1989 | Box et al. | |
| 4,846,193 A | 7/1989 | Tremulis et al. | |
| 4,863,442 A | 9/1989 | DeMello et al. | |
| 4,867,173 A | 9/1989 | Leoni | |
| 4,875,489 A | 10/1989 | Messner et al. | |
| 4,884,579 A | 12/1989 | Engelson | |
| 4,898,591 A | 2/1990 | Jang et al. | |
| 4,899,787 A | 2/1990 | Ouchi et al. | |
| 4,911,148 A | 3/1990 | Sosnowski et al. | |
| 4,917,102 A | 4/1990 | Miller et al. | |
| 4,922,164 A | 5/1990 | Jacobsen et al. | |
| 4,922,777 A | 5/1990 | Kawabata | |
| 4,932,419 A | 6/1990 | De Toledo | |
| 4,932,959 A | 6/1990 | Horzewski et al. | |
| 4,934,380 A | 6/1990 | Toledo | |
| 4,946,466 A | 8/1990 | Pinchuk et al. | |
| 4,953,553 A | 9/1990 | Tremulis | |
| 4,954,022 A | 9/1990 | Underwood et al. | |
| 4,955,384 A | 9/1990 | Taylor et al. | |
| 4,955,862 A | 9/1990 | Sepetka | |
| 4,960,410 A | 10/1990 | Pinchuk | |
| 4,964,409 A | 10/1990 | Tremulis | |
| 4,966,163 A | 10/1990 | Kraus et al. | |
| 4,968,306 A | 11/1990 | Huss et al. | |
| 4,979,951 A | 12/1990 | Simpson | |
| 4,981,478 A | 1/1991 | Evard et al. | |
| 4,985,022 A | 1/1991 | Fearnot et al. | |
| 4,989,608 A | 2/1991 | Ratner | |
| 4,990,143 A | 2/1991 | Sheridan | |
| 4,994,069 A | 2/1991 | Ritchart et al. | |
| 4,998,923 A | 3/1991 | Samson et al. | |
| 5,007,434 A | 4/1991 | Doyle et al. | |
| 5,009,137 A | 4/1991 | Dannatt | |
| 5,019,057 A | 5/1991 | Truckai | |
| 5,037,404 A | 8/1991 | Gold et al. | |
| 5,040,543 A | 8/1991 | Badera et al. | |
| 5,045,072 A | 9/1991 | Castillo et al. | |
| 5,050,606 A | 9/1991 | Tremulis | |
| 5,052,404 A | 10/1991 | Hodgson | |
| 5,057,092 A | 10/1991 | Webster, Jr. | |
| 5,059,177 A | 10/1991 | Alcebo et al. | |
| 5,063,935 A | 11/1991 | Gamble | |
| 5,065,769 A | 11/1991 | De Toledo | |
| 5,069,674 A | 12/1991 | Fearnot et al. | |
| 5,095,915 A | 3/1992 | Engelson | |
| 5,106,455 A | 4/1992 | Jacobsen et al. | |
| 5,109,830 A | 5/1992 | Cho | |
| 5,125,395 A | 6/1992 | Adair | |
| 5,135,531 A | 8/1992 | Shiber | |
| 5,144,959 A | 9/1992 | Gambale et al. | |
| 5,147,317 A | 9/1992 | Shank et al. | |
| 5,154,705 A * | 10/1992 | Fleischhacker et al. | 604/526 |
| 5,176,660 A | 1/1993 | Truckai | |
| 5,176,661 A | 1/1993 | Evard et al. | |
| 5,178,158 A | 1/1993 | De Toledo | |
| 5,180,376 A | 1/1993 | Fischell | |
| 5,181,668 A | 1/1993 | Tsuji et al. | |
| 5,184,627 A | 2/1993 | De Toledo | |
| 5,205,830 A | 4/1993 | Dassa et al. | |
| 5,211,183 A | 5/1993 | Wilson | |
| 5,217,440 A | 6/1993 | Frassica | |
| 5,217,482 A | 6/1993 | Keith | |
| 5,221,270 A | 6/1993 | Parker | |
| 5,228,441 A | 7/1993 | Lundquist | |
| 5,228,453 A * | 7/1993 | Sepetka | 600/585 |
| 5,238,004 A | 8/1993 | Sahatjian et al. | |
| 5,242,759 A | 9/1993 | Hall | |
| 5,243,996 A | 9/1993 | Hall | |
| 5,248,305 A | 9/1993 | Zdrahala | |
| 5,250,069 A | 10/1993 | Nobuyoshi et al. | |
| 5,254,106 A | 10/1993 | Feaster | |
| 5,254,107 A | 10/1993 | Soltesz | |
| 5,256,144 A | 10/1993 | Kraus et al. | |
| 5,257,974 A | 11/1993 | Cox | |
| 5,259,393 A | 11/1993 | Corso, Jr. et al. | |
| 5,267,979 A | 12/1993 | Appling et al. | |
| 5,267,982 A | 12/1993 | Sylvanowicz | |
| 5,279,562 A | 1/1994 | Sirhan et al. | |
| 5,279,596 A | 1/1994 | Castaneda et al. | |
| 5,282,484 A | 2/1994 | Reger | |
| 5,284,128 A | 2/1994 | Hart | |
| 5,300,032 A | 4/1994 | Hibbs et al. | |
| 5,304,131 A | 4/1994 | Paskar | |

| | | | | | |
|---|---|---|---|---|---|
| 5,306,244 A | 4/1994 | Shiber | 5,569,220 A | 10/1996 | Webster, Jr. |
| 5,306,252 A | 4/1994 | Yutori et al. | 5,571,073 A | 11/1996 | Castillo |
| 5,308,435 A | 5/1994 | Ruggles et al. | 5,573,520 A | 11/1996 | Schwartz et al. |
| 5,313,967 A | 5/1994 | Lieber et al. | 5,584,821 A | 12/1996 | Hobbs et al. |
| 5,315,906 A | 5/1994 | Ferenczi et al. | 5,591,142 A | 1/1997 | Van Erp |
| 5,315,996 A | 5/1994 | Lundquist | 5,599,326 A | 2/1997 | Carter |
| 5,318,032 A | 6/1994 | Lonsbury et al. | 5,599,492 A | 2/1997 | Engelson |
| 5,318,529 A | 6/1994 | Kontos | 5,601,539 A | 2/1997 | Corso, Jr. |
| 5,322,064 A | 6/1994 | Lundquist | 5,603,705 A | 2/1997 | Berg |
| 5,329,923 A | 7/1994 | Lundquist | 5,605,162 A | 2/1997 | Mirzaee et al. |
| 5,333,620 A | 8/1994 | Moutafis et al. | 5,622,184 A | 4/1997 | Ashby et al. |
| 5,334,145 A | 8/1994 | Lundquist et al. | 5,630,806 A | 5/1997 | Inagaki et al. |
| 5,334,169 A | 8/1994 | Brown et al. | 5,637,089 A | 6/1997 | Abrams et al. |
| 5,336,205 A | 8/1994 | Zenzen et al. | 5,640,970 A | 6/1997 | Arenas |
| 5,341,818 A | 8/1994 | Abrams et al. | 5,656,011 A | 8/1997 | Uihlein et al. |
| 5,345,937 A | 9/1994 | Middleman et al. | 5,656,029 A | 8/1997 | Imran et al. |
| 5,345,945 A | 9/1994 | Hodgson et al. | 5,658,263 A | 8/1997 | Dang et al. |
| 5,353,808 A | 10/1994 | Viera | 5,658,264 A | 8/1997 | Samson et al. |
| 5,354,623 A | 10/1994 | Hall | 5,662,622 A | 9/1997 | Gore et al. |
| 5,358,493 A | 10/1994 | Schweich et al. | 5,664,580 A | 9/1997 | Erickson et al. |
| 5,358,796 A | 10/1994 | Nakamura et al. | 5,666,968 A | 9/1997 | Imran et al. |
| 5,365,942 A | 11/1994 | Shank | 5,666,969 A | 9/1997 | Urick et al. |
| 5,365,943 A | 11/1994 | Jansen | 5,667,499 A | 9/1997 | Welch et al. |
| 5,368,564 A | 11/1994 | Savage | 5,669,926 A | 9/1997 | Aust et al. |
| 5,368,661 A | 11/1994 | Nakamura et al. | 5,674,208 A | 10/1997 | Berg et al. |
| 5,376,084 A | 12/1994 | Bacich et al. | 5,676,659 A | 10/1997 | McGurk |
| 5,377,690 A | 1/1995 | Berthiaume | 5,676,697 A | 10/1997 | McDonald |
| 5,381,782 A | 1/1995 | DeLaRama et al. | 5,682,894 A | 11/1997 | Orr et al. |
| 5,403,292 A | 4/1995 | Ju | 5,683,370 A | 11/1997 | Luther et al. |
| 5,406,960 A | 4/1995 | Corso, Jr. | 5,690,120 A | 11/1997 | Jacobsen et al. |
| 5,409,470 A | 4/1995 | McIntyre et al. | 5,695,506 A | 12/1997 | Pike et al. |
| 5,411,476 A | 5/1995 | Abrams | 5,702,373 A | 12/1997 | Samson |
| 5,423,773 A | 6/1995 | Jimenez | 5,706,826 A | 1/1998 | Schwager |
| 5,423,799 A | 6/1995 | Shiu | 5,720,300 A | 2/1998 | Fagan et al. |
| 5,437,288 A | 8/1995 | Schwartz et al. | 5,722,609 A | 3/1998 | Murakami |
| 5,438,993 A | 8/1995 | Lynch et al. | 5,728,063 A | 3/1998 | Preissman et al. |
| 5,439,000 A | 8/1995 | Gunderson et al. | 5,730,733 A | 3/1998 | Mortier et al. |
| 5,441,483 A | 8/1995 | Avitall | 5,738,742 A | 4/1998 | Stevens |
| 5,441,489 A | 8/1995 | Utsumi et al. | 5,741,429 A | 4/1998 | Donadio, III et al. |
| 5,447,812 A | 9/1995 | Fukuda et al. | 5,746,696 A | 5/1998 | Kondo |
| 5,451,209 A | 9/1995 | Ainsworth et al. | 5,746,701 A | 5/1998 | Noone |
| 5,454,787 A | 10/1995 | Lundquist | 5,755,704 A | 5/1998 | Lunn |
| 5,454,795 A | 10/1995 | Samson | 5,769,830 A | 6/1998 | Parker |
| 5,460,187 A | 10/1995 | Daigle et al. | 5,772,609 A | 6/1998 | Nguyen et al. |
| 5,462,523 A | 10/1995 | Samson et al. | 5,776,100 A | 7/1998 | Forman |
| 5,465,710 A | 11/1995 | Miyagi et al. | 5,779,721 A | 7/1998 | Nash |
| 5,470,330 A | 11/1995 | Goldenberg et al. | 5,782,809 A | 7/1998 | Umeno et al. |
| 5,476,701 A | 12/1995 | Berger | 5,782,811 A | 7/1998 | Samson et al. |
| 5,477,856 A | 12/1995 | Lundquist | 5,788,653 A | 8/1998 | Lorenzo |
| 5,488,959 A | 2/1996 | Ales | 5,788,654 A | 8/1998 | Schwager |
| 5,496,294 A | 3/1996 | Hergenrother et al. | 5,788,707 A | 8/1998 | Del Toro et al. |
| 5,497,783 A | 3/1996 | Urick et al. | 5,792,124 A | 8/1998 | Horrigan et al. |
| 5,497,785 A | 3/1996 | Viera | 5,795,341 A | 8/1998 | Samson |
| 5,499,973 A | 3/1996 | Saab | 5,797,856 A | 8/1998 | Frisbie et al. |
| 5,507,301 A | 4/1996 | Wasicek et al. | 5,800,454 A | 9/1998 | Jacobsen et al. |
| 5,507,729 A | 4/1996 | Lindenberg et al. | 5,807,075 A | 9/1998 | Jacobsen et al. |
| 5,507,751 A | 4/1996 | Goode et al. | 5,807,249 A | 9/1998 | Qin et al. |
| 5,507,766 A | 4/1996 | Kugo et al. | 5,810,885 A | 9/1998 | Zinger |
| 5,514,128 A | 5/1996 | Hillsman et al. | 5,813,996 A | 9/1998 | St. Germain et al. |
| 5,520,194 A | 5/1996 | Miyata et al. | 5,820,612 A | 10/1998 | Berg |
| 5,520,645 A | 5/1996 | Imran et al. | 5,827,225 A | 10/1998 | Ma Schwab |
| 5,531,719 A | 7/1996 | Takahashi | 5,827,242 A | 10/1998 | Follmer et al. |
| 5,533,985 A | 7/1996 | Wang | 5,833,632 A | 11/1998 | Jacobsen et al. |
| 5,533,987 A | 7/1996 | Pray et al. | 5,836,926 A | 11/1998 | Peterson et al. |
| 5,545,151 A | 8/1996 | O'Connor et al. | 5,843,050 A | 12/1998 | Jones et al. |
| 5,546,958 A | 8/1996 | Thorud et al. | 5,843,244 A | 12/1998 | Pelton et al. |
| 5,551,443 A * | 9/1996 | Sepetka et al. ............ 600/585 | 5,851,203 A | 12/1998 | van Muiden |
| 5,551,444 A | 9/1996 | Finlayson | 5,876,386 A | 3/1999 | Samson |
| 5,554,139 A | 9/1996 | Okajima | 5,885,207 A | 3/1999 | Iwasaka |
| 5,562,619 A | 10/1996 | Mirarchi et al. | 5,891,112 A | 4/1999 | Samson |
| 5,569,197 A | 10/1996 | Helmus et al. | 5,891,114 A | 4/1999 | Chien et al. |
| 5,569,200 A | 10/1996 | Umeno et al. | 5,895,378 A | 4/1999 | Nita |
| 5,569,218 A | 10/1996 | Berg | 5,897,537 A | 4/1999 | Berg et al. |

| | | |
|---|---|---|
| 5,899,892 A | 5/1999 | Mortier et al. |
| 5,902,254 A | 5/1999 | Magram |
| 5,902,290 A | 5/1999 | Peacock, III et al. |
| 5,904,657 A | 5/1999 | Unsworth et al. |
| 5,906,618 A | 5/1999 | Larson, III |
| 5,911,715 A | 6/1999 | Berg et al. |
| 5,911,717 A | 6/1999 | Jacobsen et al. |
| 5,916,177 A | 6/1999 | Schwager |
| 5,916,178 A | 6/1999 | Noone |
| 5,916,194 A | 6/1999 | Jacobsen et al. |
| 5,927,345 A | 7/1999 | Samson |
| 5,931,830 A | 8/1999 | Jacobsen et al. |
| 5,935,108 A | 8/1999 | Katoh et al. |
| 5,938,653 A | 8/1999 | Pepin |
| 5,947,939 A | 9/1999 | Mortier et al. |
| 5,947,940 A | 9/1999 | Beisel |
| 5,951,496 A | 9/1999 | Willi |
| 5,951,539 A | 9/1999 | Nita et al. |
| 5,954,651 A | 9/1999 | Berg et al. |
| 5,957,910 A | 9/1999 | Holden, II et al. |
| 5,971,975 A | 10/1999 | Mills et al. |
| 5,972,019 A | 10/1999 | Engelson et al. |
| 5,980,471 A | 11/1999 | Jafari |
| 5,984,877 A | 11/1999 | Fleischhacker, Jr. |
| 6,001,068 A | 12/1999 | Uchino et al. |
| 6,004,279 A | 12/1999 | Crowley et al. |
| 6,014,919 A | 1/2000 | Jacobsen et al. |
| 6,017,319 A | 1/2000 | Jacobsen et al. |
| 6,017,335 A | 1/2000 | Burnham |
| 6,019,772 A | 2/2000 | Shefram et al. |
| 6,022,343 A | 2/2000 | Johnson et al. |
| 6,022,369 A | 2/2000 | Jacobsen et al. |
| 6,024,730 A | 2/2000 | Pagan |
| 6,027,461 A | 2/2000 | Walker et al. |
| 6,030,371 A | 2/2000 | Pursley |
| 6,042,553 A | 3/2000 | Solar et al. |
| 6,042,578 A | 3/2000 | Dinh et al. |
| 6,045,547 A | 4/2000 | Ren et al. |
| 6,048,339 A | 4/2000 | Zirps et al. |
| 6,053,904 A | 4/2000 | Scribner et al. |
| 6,056,702 A | 5/2000 | Lorenzo |
| 6,063,101 A | 5/2000 | Jacobsen et al. |
| 6,063,200 A | 5/2000 | Jacobsen et al. |
| 6,066,361 A | 5/2000 | Jacobsen et al. |
| 6,099,561 A | 8/2000 | Alt |
| 6,102,890 A | 8/2000 | Stivland et al. |
| 6,106,485 A | 8/2000 | McMahon |
| 6,106,488 A | 8/2000 | Fleming et al. |
| 6,112,771 A | 9/2000 | Anyagi et al. |
| 6,139,510 A | 10/2000 | Palermo |
| 6,143,013 A | 11/2000 | Samson et al. |
| 6,152,911 A | 11/2000 | Giannoble |
| 6,152,912 A | 11/2000 | Jansen et al. |
| 6,165,163 A | 12/2000 | Chien et al. |
| 6,165,292 A | 12/2000 | Abrams et al. |
| 6,171,295 B1 | 1/2001 | Garabedian et al. |
| 6,171,296 B1 | 1/2001 | Chow |
| 6,183,410 B1 | 2/2001 | Jacobsen et al. |
| 6,193,686 B1 | 2/2001 | Estrada et al. |
| 6,197,014 B1 | 3/2001 | Samson et al. |
| 6,203,485 B1 | 3/2001 | Urick |
| 6,203,547 B1 * | 3/2001 | Nguyen et al. ............... 606/102 |
| RE37,148 E | 4/2001 | Shank |
| 6,213,995 B1 | 4/2001 | Steen et al. |
| 6,214,042 B1 | 4/2001 | Jacobsen et al. |
| 6,217,565 B1 | 4/2001 | Cohen |
| 6,228,073 B1 | 5/2001 | Noone et al. |
| 6,235,042 B1 | 5/2001 | Katzman |
| 6,245,053 B1 | 6/2001 | Benjamin |
| 6,245,068 B1 | 6/2001 | Olson et al. |
| 6,248,082 B1 | 6/2001 | Jafari |
| 6,251,092 B1 | 6/2001 | Qin et al. |
| 6,254,549 B1 | 7/2001 | Ramzipoor |
| 6,258,080 B1 | 7/2001 | Samson |
| 6,260,458 B1 | 7/2001 | Jacobsen et al. |
| 6,273,404 B1 | 8/2001 | Holman et al. |
| 6,273,876 B1 | 8/2001 | Klima et al. |
| 6,273,879 B1 | 8/2001 | Keith et al. |
| 6,290,656 B1 | 9/2001 | Boyle et al. |
| 6,290,692 B1 | 9/2001 | Klima et al. |
| 6,296,616 B1 | 10/2001 | McMahon |
| 6,296,631 B2 | 10/2001 | Chow |
| 6,302,870 B1 | 10/2001 | Jacobsen et al. |
| 6,306,105 B1 | 10/2001 | Rooney et al. |
| 6,322,534 B1 | 11/2001 | Shkolnik |
| 6,325,790 B1 | 12/2001 | Trotta |
| 6,338,725 B1 | 1/2002 | Hermann et al. |
| 6,346,091 B1 | 2/2002 | Jacobsen et al. |
| 6,348,041 B1 | 2/2002 | Klint |
| 6,352,515 B1 | 3/2002 | Anderson et al. |
| 6,355,005 B1 | 3/2002 | Powell et al. |
| 6,355,027 B1 | 3/2002 | Le et al. |
| 6,358,238 B1 | 3/2002 | Sherry |
| 6,358,256 B1 * | 3/2002 | Reinhardt ................... 606/108 |
| 6,368,315 B1 | 4/2002 | Gillis et al. |
| 6,368,316 B1 | 4/2002 | Jansen et al. |
| 6,375,628 B1 | 4/2002 | Zadno-Azizi et al. |
| 6,375,774 B1 | 4/2002 | Lunn et al. |
| 6,379,369 B1 | 4/2002 | Abrams et al. |
| 6,383,146 B1 | 5/2002 | Klint |
| 6,387,121 B1 | 5/2002 | Alt |
| 6,390,993 B1 | 5/2002 | Cornish et al. |
| 6,398,758 B1 | 6/2002 | Jacobsen et al. |
| 6,428,489 B1 | 8/2002 | Jacobsen et al. |
| 6,428,512 B1 | 8/2002 | Anderson et al. |
| 6,431,039 B1 | 8/2002 | Jacobsen et al. |
| 6,440,088 B1 | 8/2002 | Jacobsen |
| 6,443,925 B1 | 9/2002 | Schaible et al. |
| 6,458,137 B1 * | 10/2002 | Klint .......................... 606/108 |
| 6,461,311 B2 | 10/2002 | DuBois et al. |
| 6,478,778 B1 | 11/2002 | Jacobsen et al. |
| 6,485,457 B1 | 11/2002 | Hisamatsu et al. |
| 6,488,637 B1 | 12/2002 | Eder et al. |
| 6,491,648 B1 | 12/2002 | Cornish et al. |
| 6,491,671 B1 | 12/2002 | Larson, III et al. |
| 6,494,894 B2 | 12/2002 | Mirarchi |
| 6,503,244 B2 | 1/2003 | Hayman |
| 6,508,803 B1 | 1/2003 | Horikawa et al. |
| 6,508,805 B1 | 1/2003 | Garabedian et al. |
| 6,508,806 B1 | 1/2003 | Hoste |
| 6,511,462 B1 | 1/2003 | Iton et al. |
| 6,524,301 B1 | 2/2003 | Wilson et al. |
| 6,527,732 B1 | 3/2003 | Strauss et al. |
| 6,530,934 B1 | 3/2003 | Jacobsen et al. |
| 6,540,743 B2 | 4/2003 | Olson et al. |
| 6,544,197 B2 | 4/2003 | DeMello |
| 6,547,779 B2 | 4/2003 | Levine et al. |
| 6,553,880 B2 | 4/2003 | Jacobsen et al. |
| 6,556,873 B1 | 4/2003 | Smits |
| 6,562,002 B1 | 5/2003 | Taylor |
| 6,579,246 B2 | 6/2003 | Jacobsen et al. |
| 6,591,472 B1 | 7/2003 | Noone et al. |
| 6,602,207 B1 | 8/2003 | Mann et al. |
| 6,602,280 B2 | 8/2003 | Chobotov |
| 6,610,046 B1 | 8/2003 | Usami et al. |
| 6,623,448 B2 | 9/2003 | Slater |
| 6,626,889 B1 | 9/2003 | Simpson et al. |
| 6,636,758 B2 | 10/2003 | Sanchez et al. |
| 6,638,266 B2 | 10/2003 | Wilson et al. |
| 6,652,508 B2 | 11/2003 | Griffin et al. |
| 6,669,886 B1 | 12/2003 | Willard |
| 6,682,493 B2 | 1/2004 | Mirigian |
| 6,684,874 B2 | 2/2004 | Mizek et al. |
| 6,689,120 B1 | 2/2004 | Gerdts |
| 6,702,762 B2 | 3/2004 | Jafari et al. |
| 6,709,429 B1 | 3/2004 | Schaefer et al. |

| | | |
|---|---|---|
| 6,712,826 B2 | 3/2004 | Lui |
| 6,730,095 B2 | 5/2004 | Olson, Jr. et al. |
| 6,740,073 B1 | 5/2004 | Saville |
| 6,749,560 B1 | 6/2004 | Konstorum et al. |
| 6,766,720 B1 | 7/2004 | Jacobsen et al. |
| 6,777,644 B2 | 8/2004 | Peacock, III et al. |
| 6,811,544 B2 | 11/2004 | Schaer |
| 6,826,473 B1 | 11/2004 | Burch et al. |
| 6,837,898 B2 | 1/2005 | Boyle et al. |
| 6,846,535 B2 | 1/2005 | De Groot et al. |
| 6,866,642 B2 | 3/2005 | Kellerman et al. |
| 6,866,660 B2 | 3/2005 | Garabedian et al. |
| 6,875,949 B2 | 4/2005 | Hall |
| 6,887,235 B2 | 5/2005 | O'Connor et al. |
| 6,918,882 B2 | 7/2005 | Skujins et al. |
| 6,942,654 B1 | 9/2005 | Schaefer et al. |
| 6,991,606 B2 | 1/2006 | Kamiyama |
| 6,997,937 B2 | 2/2006 | Jacobsen et al. |
| 7,001,369 B2 | 2/2006 | Griffin et al. |
| 7,063,674 B2 | 6/2006 | Burmeister et al. |
| 7,074,197 B2 | 7/2006 | Reynolds et al. |
| 7,077,811 B2 | 7/2006 | Vrba et al. |
| 7,153,277 B2 | 12/2006 | Skujins et al. |
| 7,169,118 B2 | 1/2007 | Reynolds et al. |
| 7,182,735 B2 | 2/2007 | Shireman et al. |
| 7,438,712 B2 | 10/2008 | Chouinard |
| 7,507,229 B2 | 3/2009 | Hewitt et al. |
| 2001/0014770 A1 | 8/2001 | Olson et al. |
| 2002/0019599 A1 | 2/2002 | Rooney et al. |
| 2002/0045855 A1 | 4/2002 | Frassica |
| 2002/0072729 A1 | 6/2002 | Hoste et al. |
| 2003/0009184 A1 | 1/2003 | Pepin |
| 2003/0009208 A1 | 1/2003 | Snyder et al. |
| 2003/0032897 A1 | 2/2003 | Burmeister et al. |
| 2003/0060732 A1 | 3/2003 | Jacobsen et al. |
| 2003/0069521 A1 | 4/2003 | Reynolds et al. |
| 2003/0069522 A1 | 4/2003 | Jacobsen et al. |
| 2003/0139763 A1 | 7/2003 | Duerig et al. |
| 2003/0216668 A1 | 11/2003 | Howland et al. |
| 2004/0010194 A1 | 1/2004 | Kamiyama |
| 2004/0111044 A1 | 6/2004 | Davis et al. |
| 2004/0116831 A1 | 6/2004 | Vrba |
| 2004/0122340 A1 | 6/2004 | Vrba et al. |
| 2004/0142643 A1 | 7/2004 | Miller et al. |
| 2004/0143239 A1 | 7/2004 | Zhou et al. |
| 2004/0153049 A1 | 8/2004 | Hewitt et al. |
| 2004/0167437 A1 | 8/2004 | Sharrow et al. |
| 2004/0167441 A1 | 8/2004 | Reynolds et al. |
| 2004/0167442 A1 | 8/2004 | Shireman et al. |
| 2004/0176740 A1 | 9/2004 | Chouinard |
| 2004/0181174 A2 | 9/2004 | Davis et al. |
| 2004/0181176 A1 | 9/2004 | Jafari et al. |
| 2004/0193140 A1 | 9/2004 | Griffin et al. |
| 2005/0054950 A1 | 3/2005 | Parins |
| 2006/0100687 A1 | 5/2006 | Fahey et al. |
| 2006/0121218 A1 | 6/2006 | Obara et al. |
| 2006/0122537 A1 | 6/2006 | Reynolds et al. |
| 2006/0189896 A1 | 8/2006 | Davis et al. |
| 2006/0264904 A1 | 11/2006 | Kerby et al. |
| 2007/0083132 A1* | 4/2007 | Sharrow .................... 600/585 |
| 2007/0255183 A1 | 11/2007 | Chen |
| 2008/0021347 A1 | 1/2008 | Jacobsen et al. |
| 2008/0021348 A1 | 1/2008 | Jacobsen et al. |
| 2008/0021400 A1 | 1/2008 | Jacobsen et al. |
| 2008/0021401 A1 | 1/2008 | Jacobsen et al. |
| 2008/0021402 A1 | 1/2008 | Jacobsen et al. |
| 2008/0021403 A1 | 1/2008 | Jacobsen et al. |
| 2008/0021404 A1 | 1/2008 | Jacobsen et al. |
| 2008/0021405 A1 | 1/2008 | Jacobsen et al. |
| 2008/0021406 A1 | 1/2008 | Jacobsen et al. |
| 2008/0021407 A1 | 1/2008 | Jacobsen et al. |
| 2008/0021408 A1 | 1/2008 | Jacobsen et al. |
| 2008/0064989 A1 | 3/2008 | Chen et al. |
| 2008/0077119 A1 | 3/2008 | Snyder et al. |
| 2008/0097247 A1 | 4/2008 | Eskuri et al. |
| 2008/0147170 A1 | 6/2008 | Vrba |

FOREIGN PATENT DOCUMENTS

| | | |
|---|---|---|
| AU | 733966 | 4/1998 |
| BR | PI 9712829 | 1/2000 |
| CA | 2266685 | 5/2006 |
| CA | 2255781 | 3/2007 |
| CN | 1230914 | 10/1999 |
| DE | 2539191 | 3/1976 |
| DE | 285514 | 12/1990 |
| EP | 0 045 931 | 2/1982 |
| EP | 0 069 522 | 1/1983 |
| EP | 0 087 933 | 9/1983 |
| EP | 0 111 044 | 6/1984 |
| EP | 0 181 174 | 5/1986 |
| EP | 0 377 453 | 7/1990 |
| EP | 0 498 476 | 8/1992 |
| EP | 0 565 065 | 6/1996 |
| EP | 0732/117 | 9/1996 |
| EP | 0 747 089 | 12/1996 |
| EP | 0 778 038 | 6/1997 |
| EP | 0 778 039 | 6/1997 |
| EP | 0 778 040 | 6/1997 |
| EP | 0 812 599 | 12/1997 |
| EP | 0815894 | 1/1998 |
| EP | 0 865 772 | 9/1998 |
| EP | 0 865 773 | 9/1998 |
| EP | 0 521 595 | 5/1999 |
| EP | 0 917 885 | 5/1999 |
| EP | 0 937 481 | 8/1999 |
| EP | 0 790 066 | 4/2000 |
| EP | 0 608 853 | 4/2003 |
| EP | 0 935 947 | 12/2004 |
| EP | 1 586 274 | 10/2005 |
| EP | 0 934 141 | 11/2005 |
| GB | 2214354 | 8/1989 |
| GB | 2257269 | 1/1993 |
| JP | 58-8522 | 1/1983 |
| JP | 60091858 | 5/1985 |
| JP | 61022752 | 1/1986 |
| JP | 62023361 | 1/1987 |
| JP | 62089470 | 4/1987 |
| JP | 62299277 | 12/1987 |
| JP | 6393516 | 4/1988 |
| JP | 63-181774 | 7/1988 |
| JP | 63217966 | 9/1988 |
| JP | 1089956 | 4/1989 |
| JP | 1135363 | 5/1989 |
| JP | 1158936 | 6/1989 |
| JP | 2107268 | 4/1990 |
| JP | 3081831 | 4/1991 |
| JP | 03-122850 | 12/1991 |
| JP | 4061840 | 2/1992 |
| JP | 4099963 | 3/1992 |
| JP | 4213069 | 8/1992 |
| JP | 4213070 | 8/1992 |
| JP | 4236965 | 8/1992 |
| JP | 5149969 | 6/1993 |
| JP | 5-506806 | 10/1993 |
| JP | 5-309159 | 11/1993 |
| JP | 5-507857 | 11/1993 |
| JP | 6-501179 | 2/1994 |
| JP | 631749 | 4/1994 |
| JP | 6169996 | 6/1994 |
| JP | 6-63224 | 9/1994 |
| JP | 6312313 | 11/1994 |
| JP | 728562 | 5/1995 |
| JP | 7124164 | 5/1995 |
| JP | 7124263 | 5/1995 |
| JP | 7136280 | 5/1995 |

| | | | | | | |
|---|---|---|---|---|---|---|
| JP | 7148264 | 6/1995 | | WO | WO 94/06500 | 3/1994 |
| JP | 7505561 | 6/1995 | | WO | 9501123 | 1/1995 |
| JP | 7037199 | 7/1995 | | WO | WO 95/24236 | 9/1995 |
| JP | 7185009 | 7/1995 | | WO | WO 96/19255 | 6/1996 |
| JP | 7255855 | 10/1995 | | WO | WO 96/33763 | 10/1996 |
| JP | 7265319 | 10/1995 | | WO | WO 97/10022 | 3/1997 |
| JP | 7275366 | 10/1995 | | WO | WO 97/25914 | 7/1997 |
| JP | 751067 | 11/1995 | | WO | WO 97/37713 | 10/1997 |
| JP | 8-229888 | 9/1996 | | WO | WO 97/43949 | 11/1997 |
| JP | 8509141 | 10/1996 | | WO | WO 97/44083 | 11/1997 |
| JP | 8-317988 | 12/1996 | | WO | WO 97/44086 | 11/1997 |
| JP | 9000164 | 4/1997 | | WO | WO 98/10694 | 3/1998 |
| JP | 9-276413 | 10/1997 | | WO | WO 98/56448 | 12/1998 |
| JP | 9-294813 A | 11/1997 | | WO | WO 99/04847 | 2/1999 |
| JP | 10-118193 | 5/1998 | | WO | WO 99/11313 | 3/1999 |
| JP | 10-305039 | 11/1998 | | WO | WO 00/27303 | 5/2000 |
| JP | 10328191 | 12/1998 | | WO | WO 00/30710 | 6/2000 |
| JP | 11-226131 A | 8/1999 | | WO | WO 00/43061 | 7/2000 |
| JP | 11-267224 A | 10/1999 | | WO | WO 00/48645 | 8/2000 |
| JP | 2000-197704 A | 7/2000 | | WO | WO 00/57943 | 10/2000 |
| JP | 2000-510722 A | 8/2000 | | WO | WO 00/66199 | 11/2000 |
| JP | 2000-511083 A | 8/2000 | | WO | WO 00/67845 | 11/2000 |
| JP | 2001-500808 A | 1/2001 | | WO | WO 00/72907 | 12/2000 |
| JP | 2002-529137 A | 9/2002 | | WO | WO 01/10492 | 2/2001 |
| JP | 2002-542901 A | 12/2002 | | WO | WO 01/28620 | 4/2001 |
| JP | 2002-543896 A | 12/2002 | | WO | WO 01/36034 | 5/2001 |
| JP | 2003-517893 A | 6/2003 | | WO | 0145912 | 6/2001 |
| JP | 3649604 | 2/2005 | | WO | WO 01/45773 | 6/2001 |
| JP | 2005-534407 | 11/2005 | | WO | WO 01/93920 | 12/2001 |
| SU | 712908 | 1/1980 | | WO | WO 02/13682 | 2/2002 |
| SU | 758421 | 8/1980 | | WO | WO 02/062540 | 8/2002 |
| SU | 1529365 | 12/1989 | | WO | WO 03/004086 | 1/2003 |
| WO | WO 90/02520 | 3/1990 | | WO | WO 03/008148 | 1/2003 |
| WO | WO 91/13364 | 9/1991 | | WO | WO 2004/012804 | 2/2004 |
| WO | WO 92/04072 | 3/1992 | | WO | WO 2004/047899 | 6/2004 |
| WO | WO 92/07619 | 5/1992 | | WO | 2004110519 | 12/2004 |
| WO | WO 93/04722 | 3/1993 | | WO | 2008030959 | 3/2008 |
| WO | WO 93/11313 | 6/1993 | | | | |

* cited by examiner

US 7,841,994 B2

MEDICAL DEVICE FOR CROSSING AN OCCLUSION IN A VESSEL

FIELD OF THE INVENTION

The invention relates generally to medical devices. More specifically, the invention relates to intracorporal medical device, such as a guidewire, catheter, or the like, including structure for crossing an occlusion in a vessel or a patient.

BACKGROUND

The use of intravascular medical devices has become an effective method for treating many types of vascular disease. In general, one or more suitable intravascular devices are inserted into the vascular system of the patient and navigated through the vasculature to a desired target site. Using this method, virtually any target site in the patient's vascular system may be accessed, including the coronary, cerebral, and peripheral vasculature. Examples of therapeutic purposes for intravascular devices include percutaneous transluminal angioplasty (PTA) and percutaneous transluminal coronary angioplasty (PTCA).

When in use, intravascular devices, such as a guidewire, may enter the patient's vasculature at a convenient location and then can be urged to a target region in the anatomy. The path taken within the anatomy of a patient may be very tortuous, and as such, it may be desirable to combine a number of performance features in the intravascular device. For example, it is sometimes desirable that the device have a relatively high level of pushability and torqueability, particularly near its proximal end. It is also sometimes desirable that a device be relatively flexible, particularly near its distal end, for example, to aid in steering.

In addition, medical devices, such as a guidewire, catheter, or the like, will sometimes confront an occlusion, such as a lesion and/or stenosis when passing through the vasculature to a target location. In some cases, the occlusion may completely block the vessel as is the case with a chronic total occlusion. The success of the procedure often depends on the ability to insert the medical device through the occlusion.

A number of different elongated medical device structures, assemblies, and methods are known, each having certain advantages and disadvantages. However, there is an ongoing need to provide alternative elongated medical device structures, assemblies, and methods. In particular, there is an ongoing need to provide alternative medical devices including structure or assemblies configured to aid in crossing an occlusion in a vessel of a patient, and methods of making and using such structures and/or assemblies.

BRIEF SUMMARY

The invention provides design, material, manufacturing method, and use alternatives for medical devices. An example medical device includes an elongated core member including an outer surface, an intermediate member including an outer surface, the intermediate member disposed about at least a portion of the outer surface of the core member, and a coil disposed about at least a portion of the outer surface of the intermediate member. At least a portion of an outer surface of the distal region of the coil can include an undulating outer surface. The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
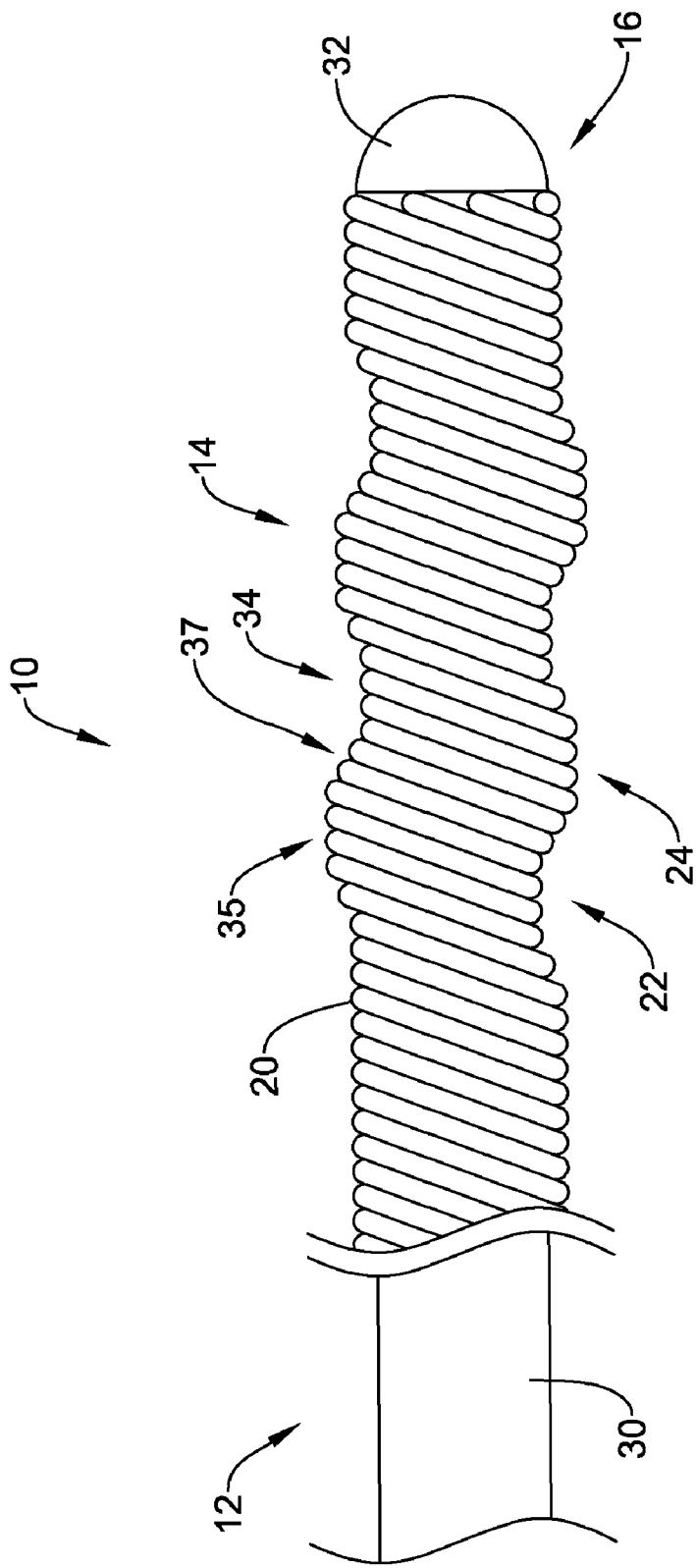
FIG. 1 is a partial perspective view of one embodiment of a guidewire.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Referring now to FIG. 1, which is a perspective view of a medical device in accordance with one illustrative embodiment. In the embodiment shown, the medical device is in the form of a guidewire 10. In one case, the guidewire 10 may be a crossing wire that can be used to aid in crossing an occlusion in a vessel of a patient, as will be discussed in more detail below. In the illustrative embodiment, guidewire 10 can include a proximal region 12 and a distal region 14 having a distal end 16. As used herein, the proximal region 12 and the distal region 14 may generically refer to any two adjacent guidewire sections along any portion of the guidewire 10.

In the illustrative embodiment, the guidewire 10 includes a coil 20 disposed about an elongated core member 30 in at least a portion of the distal region 14 of the guidewire 10. Although not depicted in FIG. 1, an intermediate member may be disposed intermediate the core member 30 and the coil 20. The coil 20 can include a number of windings defining an outer surface of the coil 20. As illustrated, the outer surface of the coil 20 has an undulating outer surface. The intermediate member may help to define, at least in part, the undulating outer surface of the coil 20.

In the illustrative embodiment, the undulating outer surface of the coil 20 may be defined by one or more recessed portions 22 and/or one or more protruding or bulging portions 24. The one or more recessed portions 22 may be defined by one or more coil windings having a recessed position relative to the other coil winding. Similarly, the one or more protruding portions 24 may be defined by one or more coil windings having a protruding position relative to the other coil windings. In some embodiments, the one or more recessed portions 22 and/or one or more protruding portions 24 can be connected by one or more coil windings extending between the one or more recessed portion 22 and the one or more protruding portion 24. In some embodiments, the one or more recessed portions 22 and/or one or more protruding portions 24 can define a groove 34 or protrusion 35 on the outer surface of the coil 20. One example groove 34 or protrusion 35 may be a helical or spiral shaped groove 34 or protrusion 35. In one example, the groove 34 and/or protrusion 35 may define a threading on the outer surface of coil 20. The threading may include one or more side surfaces at an angle relative to the one or more recessed portions 22 and the one or more protruding portions 24 defined by the one or more coil winding extending between the one or more recessed portions 22 and the one or more protruding portions 24. However, any suitable shaped groove 34 or protrusion 35 may be used, as desired.

In some embodiments, the undulating outer surface of the coil 20 is provided in the distal region 14 of the guidewire 10 proximal the distal end 16. However, the undulating outer surface of the coil 20 may be provided at any suitable position in the distal region 14 of the guidewire 10, or, more generally, in any suitable position along the length of the guidewire 10, as desired.

As illustrated, the undulating outer surface of the coil 20 has groove 34 and protrusion 35 helically disposed in the outer surface of the coil 20. In the example embodiment, the groove 34 and/or protrusion 35 may extend around the coil 20 a plurality of times. However, groove 34 and/or protrusion 35 could also extend around the coil 20 less than one revolution, one revolution, or more than one revolution, as desired. Furthermore, as illustrated, the groove 34 and/or protrusion 35 may be spaced a substantially constant distance from the longitudinal axis of the core member 30. For example, groove 34 may be spaced at a first distance from the longitudinal axis along the length of groove 34 and/or protrusion 35 may be spaced a second distance from the longitudinal axis along the length of protrusion 35. In some cases, the second distance may be greater than the first distance. However, it is contemplated that groove 34 and/or protrusion 35 may vary in distance from the longitudinal axis, as desired, for example, tapering, or decreasing the distance from the longitudinal axis, towards the distal end.

In the illustrative embodiment, guidewire 10 also includes a distal tip member 32 disposed at the distal end 16 of the guidewire 10 and/or the distal end of the coil 20. The distal tip member 32 may be any of a broad variety of suitable structures, for example, a solder tip, a weld tip, a pre-made or pre-formed metallic or polymer structure, or the like, that is attached or joined to the distal end of the coil 20 using a suitable attachment technique. In some embodiments, the distal tip member 32 may help to secure the coil windings together.

Figure 2:
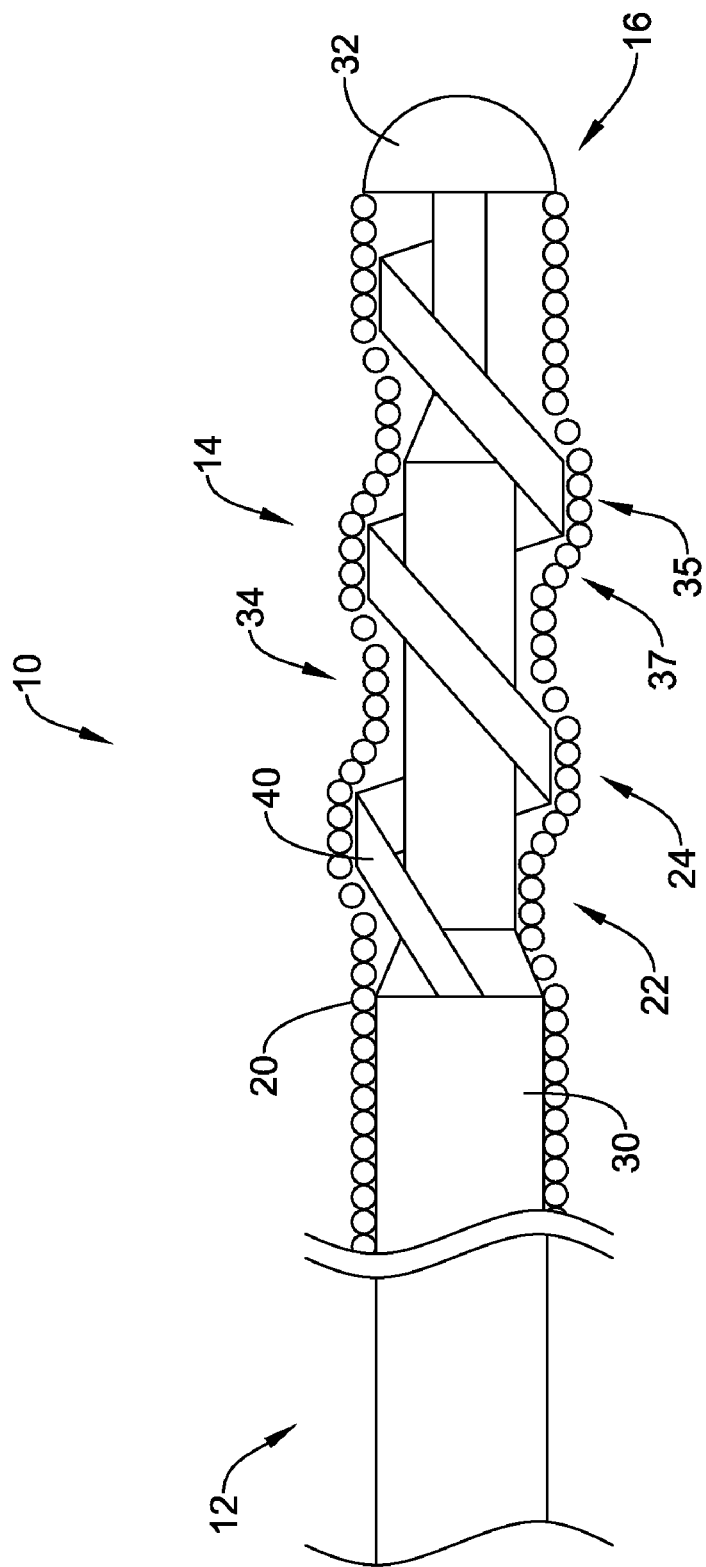
FIG. 2 is a partial cross-sectional view of the guidewire of FIG. 1.

Referring now to FIG. 2, which is a partial cross-sectional view of the guidewire 10 of FIG. 1. In this embodiment, the guidewire 10 includes a core member 30, an intermediate member 40, and a coil 20. As illustrated, the intermediate member 40 may be disposed about at least a portion of the core member 30 and the coil 20 may be disposed about at least a portion of the intermediate member 40 and/or the core member 30. The coil 20 may be disposed about the intermediate member 40 such that the coil 20 substantially tracks at least a portion of the outer surface of the intermediate member 40. In this configuration, the intermediate member 40 helps to define the undulating and/or oscillating outer surface of the coil 20.

In the illustrative embodiment, the core member 30 includes a proximal portion, a distal portion, and a longitudinal axis therethrough. In some embodiments, core member 30 may extend along the longitudinal axis and the coil 20 may include an outer surface having portions that are at an angle and/or offset from the longitudinal axis.

In some embodiments, the core member 30 can have a solid cross-section, for example a core wire, but in some embodiments, can have a hollow cross-section. In yet other embodiments, core member 30 can include a combination of areas having solid cross-sections and hollow cross sections. Moreover, core member 30, or portions thereof, can be made of rounded wire, flattened ribbon, or other such structures having various cross-sectional geometries. The cross-sectional geometries along the length of core member 30 can also be constant or can vary. For example, the illustrative embodiment depicts core member 30 as having a round cross-sectional shape. It can be appreciated that other cross-sectional shapes or combinations of shapes may be utilized without departing from the spirit of the invention. For example, the cross-sectional shape of core member 30 may be oval, rectangular, square, polygonal, and the like, or any suitable shape.

In some embodiments, the core member 30 may include a longitudinal axis therethrough. In one example embodiment, the core member 30 can be disposed concentric with the longitudinal axis, if desired. In other words, at a given point along the length of the core member 30, the center of the core member 30 may be aligned with the longitudinal axis. However, this is not required. In some examples, core member 30 may be concentric with the longitudinal axis and may include one or more tapers or tapered regions, if desired. In other cases, the core member 30 may have an outer surface that may be substantially smooth or substantially non-undulating, with the exception of the tapers.

Furthermore, the core member 30 may include one or more tapered portions, for example, to provide for desired flexibility characteristics. Such tapers can be made or exist in a linear, stepwise, curvilinear, or other suitable fashion to achieve the desired results. For example, in the embodiment shown in FIG. 2, the core member 30 includes a plurality of tapered sections and constant diameter sections. However, any tapers may be used, as desired.

The core member 30 may include a material to impart flexibility and stiffness characteristics according to the desired application. In the illustrative embodiment, core member 30 may include a material to impart stiffness and pushability in the guidewire 10. For example, the core member 30 may include a rigid and resilient material. In such an embodiment, the core member 30 may be made from a metal, a metal alloy, a polymer, a metal-polymer composite, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®, and the like), other nickel-chromium alloys, other nickel-molybdenum alloys, other nickel-cobalt alloys, other nickel-iron alloys, other nickel-copper alloys, other nickel-tungsten or tungsten alloys, and the like; cobalt alloys, such as cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material. However, this is not meant to be limiting and it is to be understood that the core member 30 may include any suitable material described herein with reference to any other guidewire component or any suitable material commonly used in medical devices, as desired.

In the illustrative embodiment, the guidewire 10 also includes the intermediate member 40 disposed intermediate of the core member 30 and the coil 20. In the illustrative embodiment, the intermediate member 40 may be a flattened wire or ribbon. However, it is to be understood that any suitable component may be used as the intermediate member 40, as desired. As illustrated, the ribbon 40 is disposed about a portion of the distal portion of the core member 20. For example, the ribbon 40 is disposed about the tapered portions of the core member 30. However, ribbon 40 may be disposed about any portion of the core member 30, as desired. Additionally, in some embodiments, the ribbon 40 may extend distally past the distal end of the core member 30, if desired.

As shown in FIG. 2, the ribbon 40 is formed with a relatively constant pitch. However, the pitch of the ribbon 40 can be varied along the length of the core member 30, if desired. For example, the pitch of the ribbon 40 could increase in the distal direction, increase in the proximal direction, or the pitch could be increased along one or more intermediate portions of the ribbon 40. Additionally, as illustrated, the ribbon has a loose or open pitch. However, the pitch depicted is illustrative and it may be varied to be any desired pitch. In addition, the thickness and the width of the ribbon 40 may also be varied according to a desired undulating and/or oscillating outer surface of the coil 20.

In this example embodiment, the ribbon 40 extends around the core member 30 a plurality of times. However, ribbon 40 could also extend around the core member 30 less than one revolution, one revolution, or more than one revolution, as desired. Furthermore, as illustrated, the ribbon 40 is wound about the core member at a relatively constant distance from the longitudinal axis of the core member 30. However, the ribbon 40 may be wound about the core member 30 at varying distances from the longitudinal axis, such as, for example, tapering in the distal direction or in the proximal direction.

Further, the ribbon 40 may be wound about the core member 30 in a position offset from the longitudinal axis, as desired.

In the illustrative embodiment, the ribbon 40 may be coupled to at least a portion of the core member 30. For example, a proximal end of the ribbon 40 may be attached to core member 30. In one example embodiment, the proximal end of the ribbon 40 may be attached to the core member 30 adjacent to the proximal end of the tapered portion. However, it is to be understood that any suitable portion of the ribbon 40 may be coupled to the core member 30 at any suitable location along the length of the core member 30, as desired.

The ribbon 40, or any other suitable intermediate member, may include a material that may import flexibility into the distal region 14 of the guidewire 10. The flexibility may help to mitigate the deformation of the core member 30. There are numerous materials that can be used for the ribbon 40 of guidewire 10 to achieve the desired properties that are commonly associated with medical devices. Some examples can include metals, metal alloys, polymers, metal-polymer composites, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®, and the like), other nickel-chromium alloys, other nickel-molybdenum alloys, other nickel-cobalt alloys, other nickel-iron alloys, other nickel-copper alloys, other nickel-tungsten or tungsten alloys, and the like; cobalt alloys, such as cobalt-chromium alloys; cobalt-chromium-molybdenum alloys (e.g., UNS: R30003 such as ELGILOY®, PHYNOX®, and the like); platinum enriched stainless steel; combinations thereof, and the like; or any other suitable material. However, this is not meant to be limiting and it is to be understood that the ribbon 40 may include any suitable material described herein with reference to any other guidewire component or any suitable material commonly used in medical devices, as desired.

Within the family of commercially available nickel-titanium or nitinol alloys, is a category designated "linear elastic" which, although it may be similar in chemistry to conventional shape memory and superelastic varieties, exhibits distinct and useful mechanical properties. By the applications of cold work, directional stress, and heat treatment, the material is fabricated in such a way that it does not display a substantial "superelastic plateau" or "flag region" in its stress/strain curve. Instead, as recoverable strain increases, the stress continues to increase in a generally linear relationship (as compared to that of super-elastic material, which has a super-elastic plateau) until plastic deformation begins. In some embodiments, the linear elastic nickel-titanium alloy is an alloy that does not show any substantial martensite/austenite phase changes that are detectable by DSC and DMTA analysis over a large temperature range.

For example, in some embodiments, there are no substantial martensite/austenite phase changes detectable by DSC and DMTA analysis in the range of about −60° C. to about 120° C. The mechanical bending properties of such material are therefore generally inert to the effect of temperature over this very broad range of temperature. In some particular embodiments, the mechanical properties of the alloy at ambient or room temperature are substantially the same as the mechanical properties at body temperature. In some embodiments, the use of the linear elastic nickel-titanium alloy allows the guidewire to exhibit superior "pushability" around tortuous anatomy. Accordingly, components of guidewire 10 such as ribbon 40 may include linear elastic nickel-titanium alloy.

In some embodiments, the linear elastic nickel-titanium alloy is in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. In some other embodiments, a superelastic alloy, for example superelastic nitinol can be used to achieve desired properties. However, it is to be understood that the above mentioned materials are not meant to be limiting and it is to be understood that the ribbon 40 may include any suitable material described herein with reference to any other guidewire component or any suitable material commonly used in medical devices, as desired.

In one example, the core member 30 includes stainless steel and the ribbon 40 includes linear elastic nitinol. In another embodiment, the core member 30 includes stainless steel and the ribbon 40 includes superelastic nitinol. In yet another embodiment, the core member 30 can have a proximal section including stainless steel and a distal section including either linear elastic and/or superelastic nitinol, and the ribbon 40 can include either linear elastic and/or superelastic nitinol. One particular advantage of having a nitinol ribbon 40 disposed about a stainless steel core member 30 may be that the nitinol may mitigate the deformation of the stainless steel core member 30 in the distal region 14 of the guidewire 10. In some cases, such a guidewire 10 may have a desired pushability and a desired tip deformation resistance for occlusion crossing application. However, it is to be understood that any material or combination of materials may be used for any application, as desired.

For example, if a nitinol ribbon is used, the ribbon 40 can be formed using any one of the numerous techniques commonly used to form such material. One example technique for shaping the ribbon may be a wind-stretch-heat set technique. In this technique, the nitinol ribbon may be shaped to have a helical winding having a loose pitch. To achieve this configuration, first, the ribbon may be tightly wound in a helical configuration. Then, the tightly wound ribbon may be longitudinally stretched to create an open pitch. In this configuration, the ribbon may be annealed or heated to set the shape of the ribbon and to cause the ribbon to remember that shape. However, it is contemplated that any other suitable technique of shaping nitinol or a like material may be used, as desired.

The illustrative embodiment includes a coil 20 wound about at least a portion of the ribbon 40 and the core member 30. As discussed previously, the coil 20 may include a number of windings defining the outer surface of the coil 20. In some embodiments, the coil may include a single coil filament having a number of windings. Alternatively, in the illustrative embodiment, the coil 20 may include a plurality of coil filaments each having a number of windings. Furthermore, the coil 20 may extend over the core member 30 and the ribbon 40 for the full length of the guidewire 10, in the distal region 14 of the guidewire 10, or over any suitable portion of the guidewire 10, as desired.

As illustrated, the coil 20 may be disposed over the ribbon 40 and the core member 30 such that the coil 20 tracks the outer surface of the ribbon 40 and the outer surface of the core member 30 to define, in part, an undulating outer surface of the coil 20. In some cases, the undulating outer surface may include one or more recesses 22 and/or one or more protruding portions 24. The one or more recesses 22 and/or one or more protruding portions 24 may define the outer surface of the coil 20 and, in some cases, may define a helical shaped groove 34 in the outer surface of the coil 20.

In the illustrative embodiment, the helical groove 34 in the outer surface of the coil 20 may form an auger-like or screw-like formation in the distal region 14 of the guidewire 10. The auger-like or screw-like formation may help to manipulate the guidewire 10 through an occlusion and advance the guidewire 10 through the occlusion, as will be discussed in greater detail with reference to FIGS. 3-5.

In the illustrative embodiment, the coil 20 may include a resilient metal. For example, the coil 20 may include those materials that are commonly used in medical device coils. For example, coil 20 may be made from a metal, a metal alloy, a polymer, a metal-polymer composite, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®, and the like), other nickel-chromium alloys, other nickel-molybdenum alloys, other nickel-cobalt alloys, other nickel-iron alloys, other nickel-copper alloys, other nickel-tungsten or tungsten alloys, and the like; cobalt alloys, such as cobalt-chromium alloys; cobalt-chromium-molybdenum alloys (e.g., UNS: R30003 such as ELGILOY®, PHYNOX®, and the like); platinum enriched stainless steel; combinations thereof, and the like; or any other suitable material. However, this is not meant to be limiting and it is to be understood that the coil 20 may include any suitable material described herein with reference to any other guidewire component or any suitable material commonly used in medical devices, as desired.

In addition, it should be understood that other structure or components, may be incorporated in the guidewire, such as a shaping wire or ribbon, one or more coils, marker members, or the like, or others, some of which are discussed below.

Figure 3:
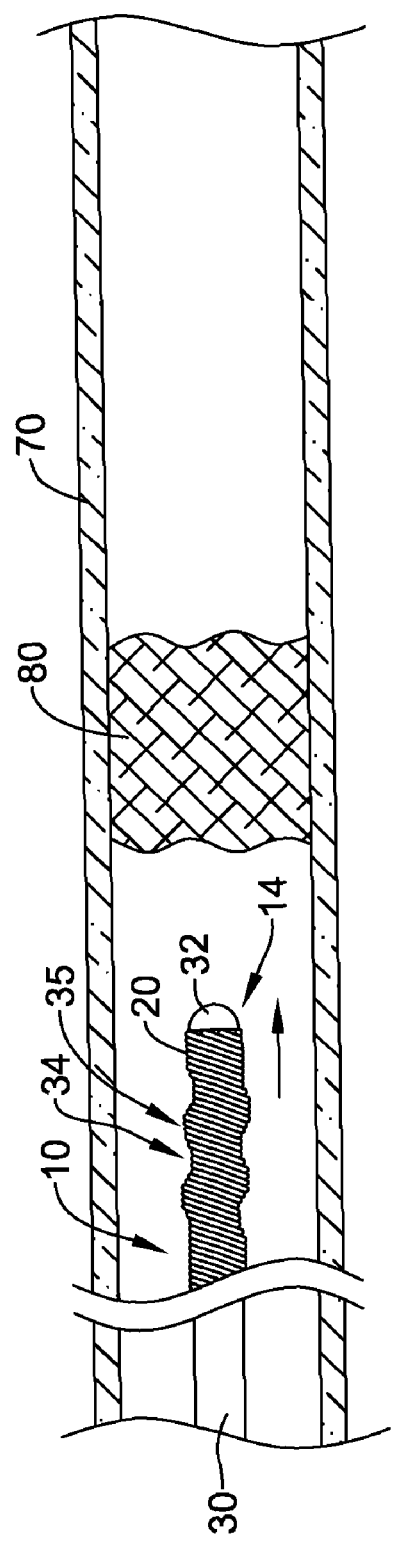
FIG. 3 is a partial cross-sectional view of a vessel including an occlusion disposed therein with the guidewire of FIG. 1 disposed within the vessel and being advanced toward the occlusion.
Figure 4:
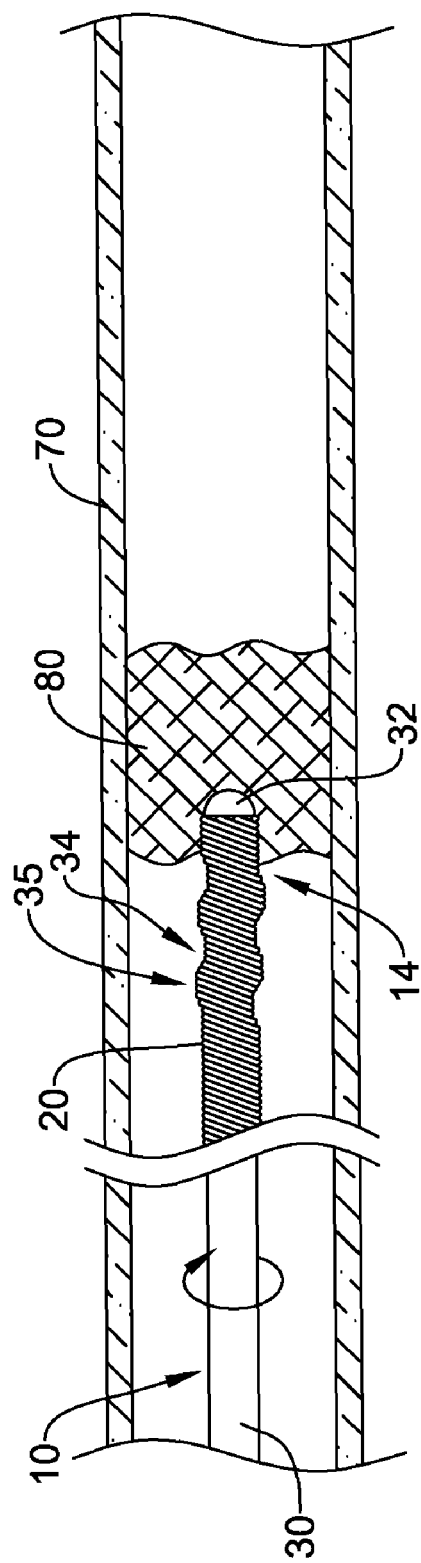
FIG. 4 is a view similar to that shown in FIG. 3, but with the distal section of the guidewire engaging the occlusion and being rotated to advance into the occlusion.
Figure 5:
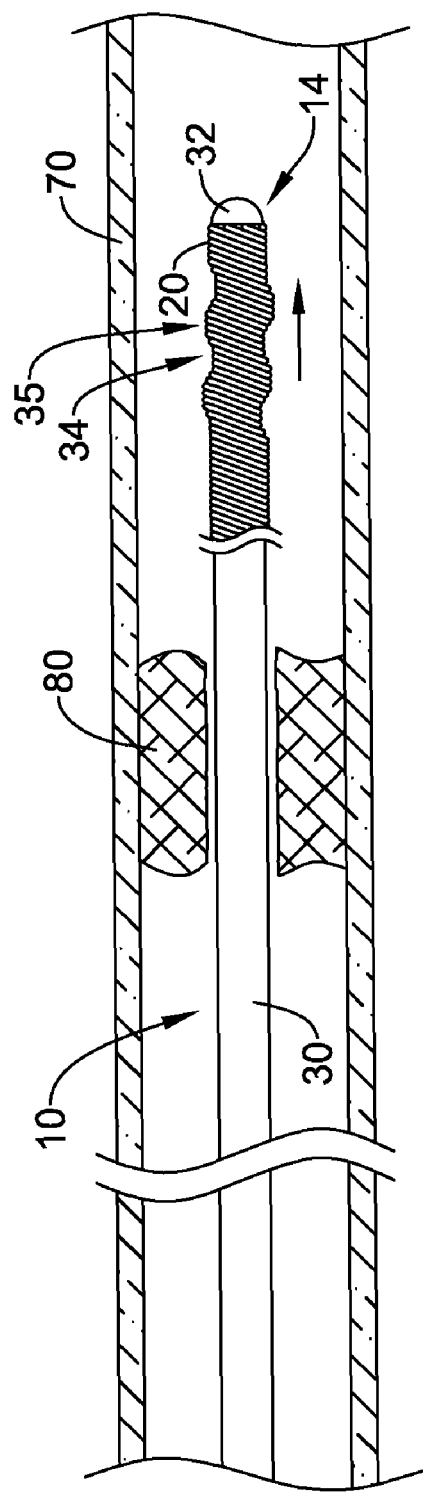
FIG. 5 is a view similar to that shown in FIG. 3, but showing the guidewire extending through the occlusion.

Referring now to FIGS. 3-5, which may be used in providing a discussion of one example of use of the guidewire 10. As mentioned above, the guidewire 10 may be configured to aid a user to cross an occlusion 80 in a vessel 70 of a patient. In particular, the groove 34 and/or helical protrusion 35 defined in the outer surface of the coil 20 by the intermediate member of the guidewire 10 may be configured to aid in drawing and/or pulling the guidewire 10 into and/or through an occlusion. As shown in FIG. 3, the guidewire 10 may be advanced through the patient's vasculature, for example in a vessel 70, until it reaches an occlusion 80 within the vessel 70. As shown in FIG. 4, the distal region 14 of the guidewire 10, in particular, the distal tip 32, may be forced into contact with the occlusion 80. For example, the distal region 14 may be pushed slightly into the occlusion 80. As indicated by the circular arrow in FIG. 4, the guidewire 10 may be rotated such that at least part of the helical-shaped groove 34 and/or helical protrusion 35 in the outer surface of the coil 20 engages a portion of the occlusion 80. As the guidewire 10 is rotated in a direction to assist insertion, the groove 34 and/or helical protrusion 35 can engage the occlusion in a screw-like, auger-like, and/or threaded-like manner and draw and/or pull the guidewire 10 into the occlusion 80. Continued application of rotational force, in some cases in combination with lateral force, may allow the distal section to continue to screw and/or auger into the occlusion, and ultimately pass through the occlusion, as shown in FIG. 5. As illustrated, the guidewire 10 may have a groove 34 and/or helical protrusion 35 with a left-handed or counter-clockwise orientation to advance it into the occlusion. However, it is contemplated that a right-handed or clockwise orientation of the groove 34 and/or helical protrusion 35 may be used, as desired. Once the guidewire 10 is passed through the occlusion, another device, such as a catheter, atherectomy device, distal protection device, or the like may be threaded onto the guidewire and urged distally and passed through the occlusion 80 and/or may be used to treat the occlusion 80.

While the foregoing has been described with reference to the groove 34 and/or helical protrusion 35 engaging a portion of the occlusion 80, it is to be understood that the groove 34 may engage a portion of the occlusion 80, the helical protrusion 35 may engage a portion of the occlusion 80, the threading defined in part by the groove 34 and/or helical protrusion 35 may engage a portion of the occlusion 80, one or more side surface of the threading or helical protrusions 35 may engage a portion of the occlusion 80, or any other suitable portion of guidewire 10 may engage a portion of the occlusion 80, as desired.

Figure 6:
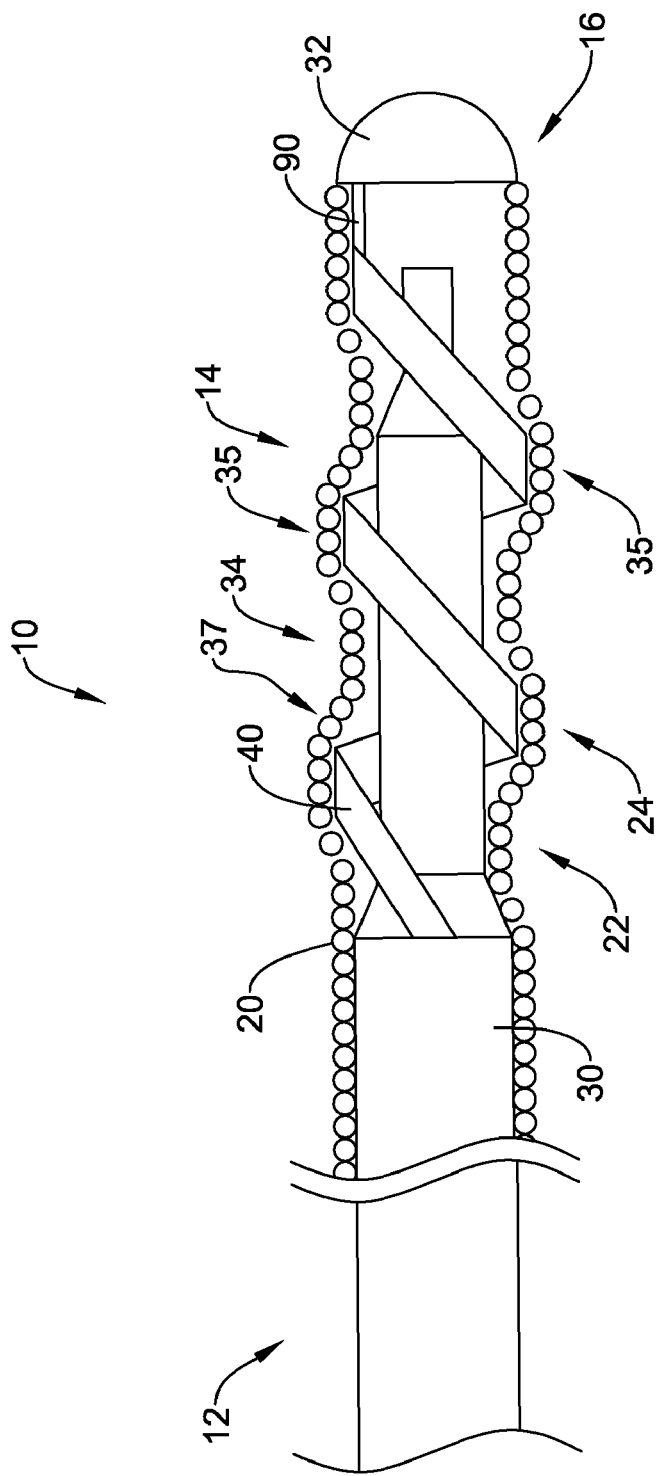
FIG. 6 is a partial cross-sectional view of an alternative guidewire embodiment.

Another embodiment is shown in FIG. 6, wherein common reference numerals can refer to similar structure to the embodiments discussed above. In this embodiment, core member 30 may have a distal end proximal of the distal tip 32. A shaping ribbon 90 may be provided extending between the distal tip 32 and the distal end of the core member 30. In this configuration, the core member 30 is not directly attached to the distal tip 32. This may allow for greater movement of the core member 30 within the coil 20 creating greater flexibility in the distal region 14 of the guidewire 10. Additionally, the incorporation of the shaping ribbon 90 may allow the distal region 14 of the guidewire 10 to be deformed or shaped by the user, as desired. Furthermore, the distal end of the ribbon 40 may be secured to the proximal end of the shaping ribbon 90, which, may have it's distal end attached to the distal tip 32.

Figure 7:
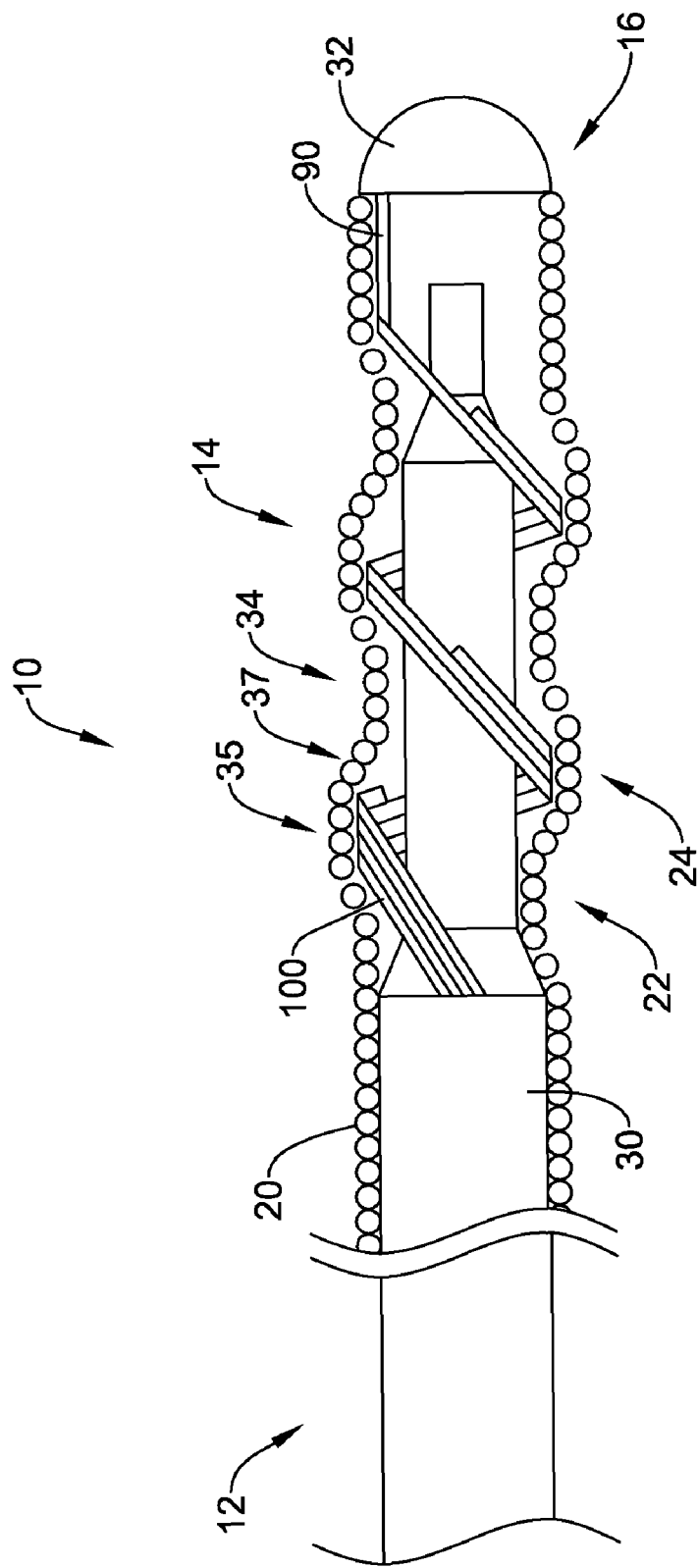
FIG. 7 is a partial cross-sectional view of another alternative guidewire embodiment.

In addition, many other configurations of the intermediate member are contemplated. For example, FIG. 7 shows another alternative embodiment of a guidewire having a multi-filar intermediate member 100. The multi-filar intermediate member 100 may be a structure, such as, for example, a wire, that includes multiple filaments. The multi-filar structure may be wound about the core member 30, similar to that as described with the ribbon of FIG. 2.

In the illustrative embodiment, the multi-filar wire 100 may be wound with a drop-filar technique. The drop-filar technique sequentially drops one of the filaments as the multi-filar wire 100 moves towards the distal end 16 of the guidewire 10. For example, in the embodiment shown, at the proximal end of the multi-filar wire 100, there are four filaments and one wire is dropped from the multi-filar wire 100 after a distance. This is continued until there is a single wire at the distal end of the multi-filar wire 100. However, it is also contemplated that the drop-filar technique may be reversed, for example, with four filaments at the distal end and one filament at the proximal end of the multi-filar wire 100. The incorporation of this technique may impart a varying degree of flexibility along the distal region 14 of the guidewire 10 and/or may affect the width of the threading (i.e. the groove and/or protrusion) on the undulating surface, for example, the width may narrow as filaments are dropped. While four filaments are shown in the example embodiment, any number of filaments may be used as desired, for example, less than four filaments, such as two or three filaments, or greater than four filaments, such as five, six, seven, eight, or more filaments. However, this technique is not required and any other suitable multi-filar wire 100 may be used with any number of filaments, as desired.

Furthermore, as illustrated, the multi-filar wire 100 has a flat outer surface adjacent the coil 20. However, in other embodiments, the multi-filar wire 100 may be a round wound multi-filar wire 100, or have any other suitable shape and configuration, as desired.

Figure 8:
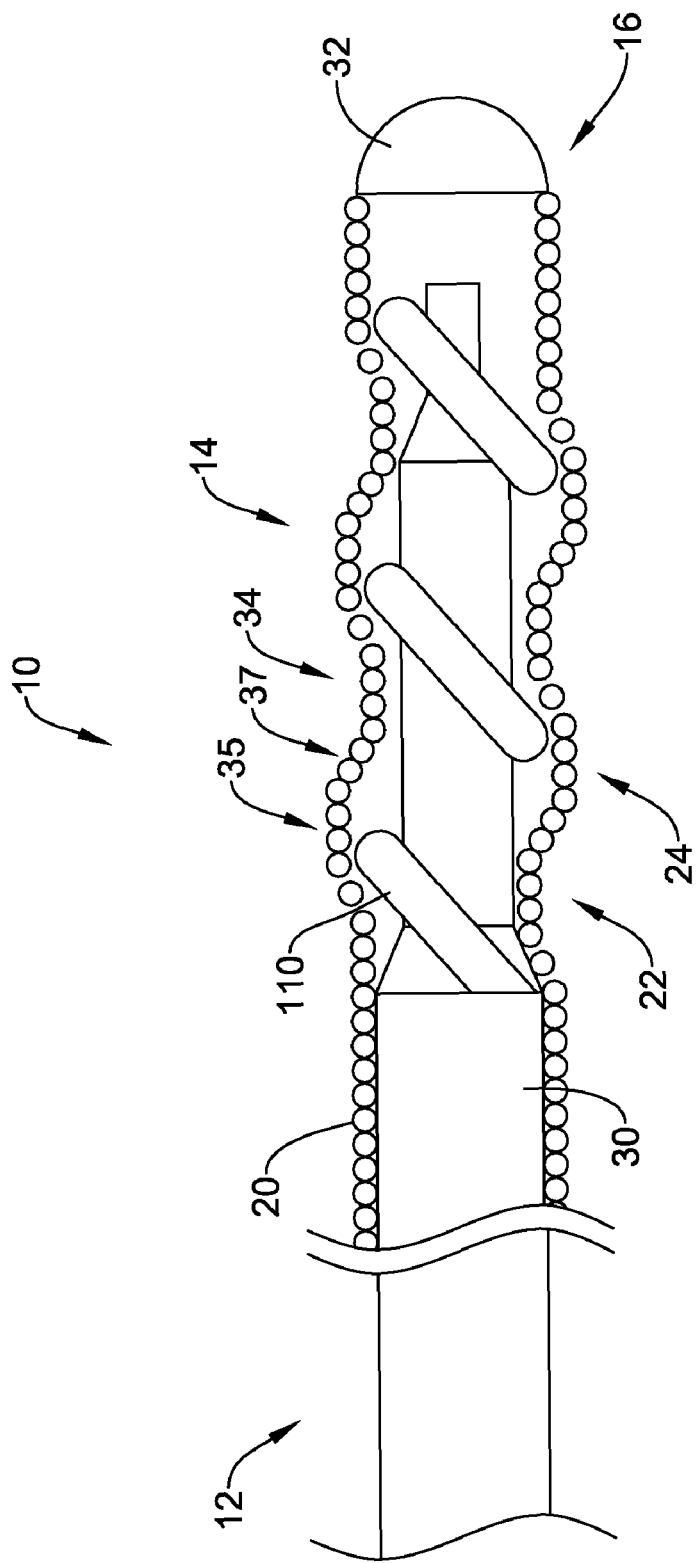
FIG. 8 is a partial cross-sectional view of another alternative guidewire embodiment.

FIG. 8 shows another example embodiment wherein common reference numbers indicate similar structure. In this embodiment, the intermediate member may include one or more individual structures, such as rings 110 disposed over the core member 30 to define an undulating outer surface of the coil 20. As illustrated, the rings 110 may be positioned at an angle to the longitudinal axis of the core member 30. However, this is not required and in another embodiment, the rings 110 may be orthogonal to the longitudinal axis of the core member 30, as desired. In addition, the rings 110 are illustrated having rounded edges, but this is not required. In other embodiments, the rings 110 may have flat edges, as desired.

The foregoing described intermediate members are meant to be illustrative of the present invention. However, this is not meant to be limiting and it is to be understood that any suitable intermediate member may be provided intermediate to the core member 30 and the coil 20 to help define an undulating outer surface in the coil 20, as desired.

In at least some embodiments, portions or all of core member 30, intermediate member 40, and/or coil 20, or other components that are part of or used in the device, may be doped with, made of, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, polymer material loaded with a radiopaque filler, and the like. Additionally, radiopaque marker bands and/or coils may be incorporated into the design of guidewire 10 to achieve the same result.

In some embodiments, a degree of MRI compatibility is imparted into device 10. For example, to enhance compatibility with Magnetic Resonance Imaging (MRI) machines, it may be desirable to make core member 30, intermediate member 40, and/or coil 20, or other portions of the medical device 10, in a manner that would impart a degree of MRI compatibility. For example, core member 30, intermediate member 40, and/or coil 20, or portions thereof, may be made of a material that does not substantially distort the image and create substantial artifacts (artifacts are gaps in the image). Certain ferromagnetic materials, for example, may not be suitable because they may create artifacts in an MRI image. Core member 30, intermediate member 40, and/or coil 20, or portions thereof, may also be made from a material that the MRI machine can image. Some materials that exhibit these characteristics include, for example, tungsten, Elgiloy, MP35N, nitinol, and the like, and others.

In some embodiments, a sheath and/or coating, for example a lubricious, a hydrophilic, a protective, or other type of material may be applied over portions or all of the core member 30, intermediate member 40 and/or coil 20, or other portions of device 10. Some examples of suitable polymer sheath materials may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

In some embodiments sheath material can be blended with a liquid crystal polymer (LCP). For example, the mixture can contain up to about 6% LCP. This has been found to enhance torqueability. By employing selection of materials and processing techniques, thermoplastic, solvent soluble, and thermosetting variants of these and other materials can be employed to achieve the desired results. Some examples of suitable coating materials may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Some coating polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. Some examples of coatings would be disposing a coating on the thread member(s) and/or all or a portion of the coil, all or a portion of the intermediate member, and/or all or a portion of the core member.

A coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

The length of the guidewire 10 is typically dictated by the length and flexibility characteristics desired in the final medical device. For example, proximal section 12 may have a length in the range of about 20 to about 300 centimeters or more, the distal section 14 may have a length in the range of about 3 to about 50 centimeters or more, and the medical device 10 may have a total length in the range of about 25 to about 350 centimeters or more. It can be appreciated that alterations in the length of sections and/or of the guidewire 10 as a whole can be made without departing from the spirit of the invention.

In some cases, core member 30 can be made of the same material along its length, or in some embodiments, can include portions or sections made of different materials. In some embodiments, the material used to construct core member 30 is chosen to impart varying flexibility and stiffness characteristics to different portions of core member 30. For example, the proximal region and the distal region of core wire 30 may be formed of different materials, for example materials having different moduli of elasticity, resulting in a difference in flexibility. In some embodiments, the material used to construct the proximal region can be relatively stiff for pushability and torqueability, and the material used to construct the distal region can be relatively flexible by comparison for better lateral trackability and steerability. For example, the proximal region can be formed of straightened 304v stainless steel wire or ribbon and the distal region can be formed of a straightened super elastic or linear elastic alloy, for example a nickel-titanium alloy wire or ribbon.

In embodiments where different portions of core member 30 are made of different materials, the different portions can be connected using any suitable connecting techniques. For example, the different portions of core member 30 can be connected using welding (including laser welding), soldering, brazing, adhesive, or the like, or combinations thereof Additionally, some embodiments can include one or more mechanical connectors or connector assemblies to connect the different portions of core member 30 that are made of different materials. The connector may include any structure generally suitable for connecting portions of a guidewire. One example of a suitable structure includes a structure such as a hypotube or a coiled wire which has an inside diameter sized appropriately to receive and connect to the ends of the proximal portion and the distal portion. Some other examples of suitable techniques and structures that can be used to interconnect different shaft sections are disclosed in U.S. patent application Ser. No. 09/972,276 filed on Oct. 5, 2001, Ser. No. 10/068,992 filed on Feb. 28, 2002, and Ser. No. 10/375,766 filed on Feb. 26, 2003, which are incorporated herein by reference.

It should also be understood that a broad variety of other structures and/or components may be used in the guidewire construction. Some examples of other structures that may be used in the guidewire 10 include one or more coil members, braids, shaping or safety structures, such as a shaping ribbon or wire, marker members, such as marker bands or coils, centering structures for centering the core wire within the tubular member, such as a centering ring, an extension system, for example, to effectively lengthen the guidewire for aiding in exchanging other devices, or the like, or other structures. Those of skill in the art and others will recognize that the materials, structure, and dimensions of the guidewire may be dictated primary by the desired characteristics and function of the final guidewire, and that any of a broad range of materials, structures, and dimensions can be used.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. It should be understood that this disclosure is, in many respects, only illustrative. Changes may be made in details, particularly in matters of shape, size, and arrangement of steps without exceeding the scope of the invention. For example, although set forth with specific reference to guidewires in some of the example embodiments shown in the Figures and discussed above, the invention may relate to virtually any medical device that may aid a user of the device in crossing an occlusion in a blood. For example, the invention may be applied to medical devices such as a balloon catheter, an atherectomy catheter, a drug delivery catheter, a stent delivery catheter, an endoscope, a fluid delivery device, other infusion or aspiration devices, delivery (i.e. implantation) devices, and the like. Thus, while the Figures and descriptions above are directed toward a guidewire, in other applications, sizes in terms of diameter, width, and length may vary widely, depending upon the desired properties of a particular device. The scope of the invention is, of course, defined in the language in which the appended claims are expressed.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical guidewire comprising:
   an elongated core member including an outer surface;
   an intermediate member helically surrounding at least a portion of the core member, the intermediate member including an outer surface, wherein the intermediate member is disposed at a first pitch about at least a portion of the core member; and
   a coil member surrounding at least a portion of the outer surface of the intermediate member and at least a portion of the outer surface of the core member, at least a portion of the coil member including an undulating outer surface defined by the coil member tracking the outer surface of the intermediate member, wherein the coil member is disposed at a second pitch about at least a portion of the outer surface of the intermediate member, wherein the first pitch is relatively loose compared to the second pitch, wherein the undulating outer surface has a third pitch corresponding to the first pitch of the intermediate member.

2. The medical guidewire of claim 1 wherein the undulating outer surface of the coil is further defined by the coil member tracking at least part of the outer surface of the core member.

3. The medical guidewire of claim 2 wherein the undulating outer surface of the coil includes one or more protruding portions and one or more recessed portions, the one or more protruding portions and the one or more recessed portions defining a threading structure.

4. The medical guidewire of claim 3 wherein the threading structure is helically disposed about the core member.

5. The medical guidewire of claim 1 wherein the intermediate member is a ribbon.

6. The medical guidewire of claim 1 wherein the core member includes a rigid material.

7. The medical guidewire of claim 6 wherein the rigid material is stainless steel.

8. The medical guidewire of claim 1 wherein the intermediate member includes a material having deformation resistance.

9. The medical guidewire of claim 8 wherein the intermediate member includes a nickel-titanium alloy.

10. The medical guidewire of claim 1 wherein the core member includes a distal end, and wherein the intermediate member extends to or distal of the distal end.

11. The medical guidewire of claim 1 wherein the intermediate member is a multi-filar wire.

12. The medical guidewire of claim 1 wherein the intermediate member having a length and the coil member is disposed about the outer surface of the intermediate member for the length of the intermediate member.

13. A medical guidewire comprising:
    an elongated core member including a proximal region and a distal region, the elongate member having an outer surface;
    a ribbon helically disposed about at least a portion of the outer surface of the core member, wherein the ribbon has a generally flat cross-sectional shape, the ribbon disposed at a first pitch, the ribbon having an outer surface; and
    a coil member disposed about at least a portion of the outer surface of the ribbon and at least a portion of the outer surface of the core member, the coil member disposed at a second pitch different than the first pitch, at least a portion of the coil member including an undulating outer surface defining a helical shaped threading structure having a third pitch that corresponds to the first pitch.

14. The medical guidewire of claim 13 wherein the ribbon is helically disposed about the core member in at least a portion of the distal region.

15. The medical guidewire of claim 13 wherein the undulating outer surface of the coil is defined in part of the outer surface of the core member.

16. The medical guidewire of claim 15 wherein the coil tracks at least a portion of the ribbon and at least a portion of the core member to define the undulating outer surface.

17. The medical guidewire of claim 13 wherein the helical shaped threading structure includes one or more protruding portions and one or more recessed portions.

18. A medical guidewire comprising:
    an elongated core member including an outer surface;
    an intermediate member helically surrounding at least a portion of the core member, the intermediate member including an outer surface, wherein the intermediate member is disposed at a first pitch around at least a portion of the core member, the intermediate member having a length; and
    a coil member surrounding the outer surface of the intermediate member for the length of the intermediate member and at least a portion of the outer surface of the core member, at least a portion of the coil member including an undulating outer surface defined by one or more windings of the coil member having a radially offset position relative to other windings of the coil member, the coil member tracking the outer surface of the intermediate member, wherein the coil member is disposed at a second pitch around the outer surface of the intermediate member, wherein the first pitch is relatively loose compared to the second pitch.

19. The medical guidewire of claim 18 wherein the intermediate member is a ribbon.

20. The medical guidewire of claim 18 wherein the intermediate member is a coil.

21. The medical guidewire of claim 18 wherein the core member includes a distal end, and wherein the intermediate member extends to or distal of the distal end.

22. The medical guidewire of claim 18 wherein the one or more windings of the coil member having a radially offset position relative to other windings of the coil member include one or more protruding portions and one or more recessed portions, the one or more protruding portions and the one or more recessed portions defining a helical threading structure.

23. A medical guidewire comprising:
an elongated core member including a proximal region and a distal region, the elongate core member including an outer surface, wherein the elongate core member has one or more tapered portions in the distal region.;
an intermediate member helically surrounding at least a portion of the core member, the intermediate member including an outer surface, wherein the intermediate member includes a proximal end disposed adjacent to or distal of a proximal end of the one or more tapered portions of the distal region of the elongate core member; and
a coil member surrounding the outer surface of the intermediate member and at least a portion of the outer surface of the core member, wherein the coil member includes a proximal end disposed proximal of the proximal end of the intermediate member and a distal end disposed adjacent to or distal of the distal end of the intermediate member, at least a portion of the coil member including an undulating outer surface defined by the coil member tracking the outer surface of the intermediate member such that, along a cross-section of the guidewire, the coil member is disposed at a non-uniform radial distance from the outer surface of the elongate member.

24. The medical guidewire of claim 23 wherein the intermediate member is disposed at a first pitch around at least a portion of the core member.

25. The medical guidewire of claim 24 wherein the coil member is disposed at a second pitch around at least a portion of the outer surface of the intermediate member and at least a portion of the outer surface of the core member, wherein the first pitch is relatively loose compared to the second pitch.

26. The medical guidewire of claim 23 wherein the intermediate member is a ribbon.

27. A medical guidewire comprising:
an elongated core member including a proximal region and a distal region, the elongate member having an outer surface;
a ribbon helically disposed about at least a portion of the outer surface of the core member, wherein the ribbon has a generally flat cross-sectional shape, the ribbon disposed at a first pitch, the ribbon having an outer surface; and
a coil member including rounded edges wound around at least a portion of the outer surface of the ribbon and at least a portion of the outer surface of the core member, the coil member disposed at a second pitch different than the first pitch, an outer surface of the coil member including first undulations defined by the rounded edges of the coil member, the first undulations having the second pitch, the outer surface of the coil member including second undulations defined at least in part by the ribbon, the second undulations having a third pitch corresponding to the first pitch.

28. The medical guidewire of claim 27, wherein the second undulations are larger than the first undulations, wherein the second undulations include one or more protruding portions and one or more recessed portions defining a helical threading structure.

* * * * *